(12) United States Patent
Ogino et al.

(10) Patent No.: US 6,600,014 B2
(45) Date of Patent: *Jul. 29, 2003

(54) ADSORBENT FOR ELIMINATING HEPATITIS C VIRUS, ADSORBER, AND ADSORPTION METHOD

(75) Inventors: Eiji Ogino, Kobe (JP); Michio Nomura, Kakogawa (JP); Takashi Asahi, Kobe (JP); Shuichi Kaneko, Kanazawa (JP); Akito Sakai, Kanazawa (JP)

(73) Assignee: Kaneka Corporation, Osaka (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/380,644
(22) PCT Filed: Mar. 25, 1998
(86) PCT No.: PCT/JP98/01317
§ 371 (c)(1),
(2), (4) Date: Nov. 9, 1999
(87) PCT Pub. No.: WO98/42392
PCT Pub. Date: Oct. 1, 1998

(65) Prior Publication Data
US 2003/0044769 A1 Mar. 6, 2003

(30) Foreign Application Priority Data
Mar. 25, 1997 (JP) .............................. 9-071483

(51) Int. Cl.$^7$ .............................................. C07K 17/00
(52) U.S. Cl. ...................... 530/324; 530/402; 530/413; 530/810; 435/239; 435/308.1; 604/5.02
(58) Field of Search .............................. 530/412, 391.1, 530/413, 390.1, 415, 402, 324, 810, 811, 812; 435/2, 236, 239, 308.1; 424/140.1; 604/5.02

(56) References Cited

U.S. PATENT DOCUMENTS

| 4,576,928 | A | * | 3/1986 | Tani et al. ................... | 502/404 |
| 4,681,870 | A | * | 7/1987 | Balint, Jr. et al. .......... | 502/403 |
| 5,037,649 | A | | 8/1991 | Balint, Jr. et al. | |
| 5,846,735 | A | * | 12/1998 | Stapleton et al. ............ | 435/7.1 |
| 6,133,431 | A | * | 10/2000 | Yasuda et al. .............. | 530/413 |
| 6,358,692 | B1 | * | 3/2002 | Jindal et al. ................ | 530/413 |

FOREIGN PATENT DOCUMENTS

| EP | 0752425 A2 | | 1/1997 | | |
| JP | 09033530 | * | 2/1997 | ......... | G01N/33/576 |
| WO | WO 90/09237 | | 8/1990 | | |

OTHER PUBLICATIONS

Sigma Immuno Chemicals. Sigma Chemical Co., St. Louis MO, p. 302–311, 1995.*
Pierce Immuno Technology Catalog & Handbook, Pierce Chemical Co., Rockford IL, p. B22–B25, B28–33, 1992.*
Vola et al. Journal of Chromatography B 668:209–218, 1995.*
Gazitt et al. Immunology Letters 11:1–8, 1995.*
Goetzl et al. Immunology 53:227–234,1984.*
Frick et al. Molecular Microbiology 12(1): 143–151, 1994.*
Heimer et al. Int J Cancer 18 (3): 310–316.1976 (Abstract only cited).*
Akesson et al. Biochemical journal (England) Jun. 15, 1994, 300 (Pt 3) p877–86 (Abstract only cited).*
Bjorck, Protein L: A Novel Bacterial Cell Wall Protein with Affinity for Ig L Chains, *The Journal of Immunology* 140 (40): 1194–1197 (Feb. 15, 1988).
Baumann et al, An Immune Complex Selective Affinity Matrix Utilizing a Synthetic Peptide, *The Journal of Biological Chemistry* 265 (30): 18414–18422 (Oct. 25, 1990).
Gomi et al, The Gene Sequence and Some Properties of Protein H: A Novel IgG–Binding Protein, *The Journal of Immunology* 144 (10): 4046–4052 (May 15, 1990).
Uhlen et al, Complete Sequence of the Staphylococcal Gene Encoding Protein A:A Gene Evolved through Multiple Duplications, *The Journal of Biological Chemistry* 259 (3): 1695–1702 (Feb. 10, 1984).
Guss et al, Structure of the IgG–Binding Regions of Stretococcal Protein G, *The EMBO Journal* 5 (7): 1567–1575, 1986.
Huston et al, Multisite Association by Recombinant Proteins can Enhance Binding Selectively, *Biophysical Journal* 62 (Discussions 1992): 87–91 (1992).
RINSYOMENEI 23 (6): 896–903 (1991).
Nihon Shokakibyogakkai Magazine 92 (Special Edition): 1488, col. 27.

* cited by examiner

*Primary Examiner*—Mary E. Mosher
(74) *Attorney, Agent, or Firm*—Connolly Bove Lodge & Hutz LLP (57) ABSTRACT

An adsorbent for removing hepatitis C virus which has the ability to adsorb HCV particles, particularly immune-complex HCV particles, from a patient's body blood safely and with high efficiency and high selectivity for enhancing the efficacy of interferon therapy, an HCV adsorption apparatus including said adsorbent, and a adsorbing method for removing HCV are provided.

An adsorbent for removing hepatitis C virus which comprises a compound capable of adsorbing hepatitis C virus as immobilized on a water-insoluble carrier, an adsorption apparatus including said adsorbent, and an adsorbing method for removing HCV.

20 Claims, 3 Drawing Sheets

ADSORBENT FOR ELIMINATING HEPATITIS C VIRUS, ADSORBER, AND ADSORPTION METHOD

TECHNICAL FIELD

The present invention relates to an adsorbent for removing hepatitis C virus which is capable of selectively adsorbing hepatitis C virus from body fluids such as blood, plasma, etc. to thereby expedite the cure for hepatitis C, an adsorption apparatus including said adsorbent, and an adsorbing method for removing hepatitis C virus.

PRIOR ART

With the successful cloning of the RNA virus genome of hepatitis C virus in 1989 (Q. L. Choo et al.: Science, 244, 359, 1989), it became possible to assay anti-hepatitis C virus antibody using a recombinant protein. As a result, most of the hepatitis termed non-A, non-B hepatitis in the past were found to be hepatitis C. Thus, it is estimated that in Japan today there are about 2,000,000 HCV carriers and, of them, 1,400,000 have chronic hepatitis and 300,000 have cirrhosis (Shiro Iino: Medical Practice in Gastroenterology-2, Hepatitis C, 11–17, 1993).

According to the Ministry of Health and welfare demographic statistics, the number of deaths due to primary liver cancer in 1992 was 27 thousand (1992 Demographic Statistics, Minister of Health and Welfare Statistical Information Bureau, Vol. 1, 1993) and approximately 70% of the casualties were due to hepatocellular carcinoma associated with hepatitis C virus infection and it is by now considered that this cancer ensues following the progression of chronic hepatitis to cirrhosis (S. Kaneko et al.: Intervirology, 37, 108, 1994; Eiki Matsushita et al.: Japanese Journal of Clinics, 53, 727, 1995 Special Issue). Therefore, hepatitis C can be said to be a refractory disease which progresses to cirrhosis to hepatocellular carcinoma.

The conventional therapy of hepatitis C is mostly built around rest cure, dietary thereby, and pharmacotherapy using hepatoprotectants and/or Chinese medicines. However, because the hepatitis virus cannot be removed by such therapeutics, the cure rate is miserably low. This is why, in clinical practice, emphasis has been placed on the arrest of progression of chronic liver disease through palliation of local tissue necrosis. Therefore, as the disease period is prolonged, many patients succumb to hepatocellular carcinoma, the serious outcome, through cirrhosis as mentioned above.

Meanwhile, the mass production of interferons became feasible recently and those proteins were found to show not only antiviral activity against hepatitis C virus and its cognate RNA viruses in vitro (Yasuyuki Ninomiya et al.: The Clinical Report, 19, 231, 1985) but also protective activity in mice infected with RNA viruses (M. Kramer et al.: J. Interferon Res., 3, 425, 1983). Accordingly, the utility of interferons in clinical cases of hepatitis C has come into the focus of attention.

Actually, serum transaminase was normalized in some of the non-A, non-B hepatitis cases which were treated with a recombinant interferon-alpha (J. H. Hoofnagel et al.: N. Eng. J. Med., 315, 1575, 1986) and in the administration of an interferon to patients with hepatitis C, some cases became consistently negative to hepatitis C virus RNA in blood (K. Chayama et al.: Hepatology, 13, 1040, 1991; Hideki Ogiwara et al.: Japanese Journal of Gastroenterology, 88, 1420, 1991). In view of those results, interferons have come to be broadly used in clinical practice. Thus, the therapy of hepatitis C has made a decisive step forward from symptomatic therapy to etiotropic therapy.

However, in the interferon therapies performed in about 200,000 cases of type C chronic active hepatitis during the past several years in Japan, it was only in about 30% of cases that the virus could be eliminated and the disease cured and in the remaining about 70% of cases the virus survived and the therapy either proved ineffective or recurrences were encountered (Migito Yano: Japanese Journal of Clinics, 53, 986, 1995 Special Issue).

In the success or failure of a therapy, the hepatitis C virus gene type, the viral population in blood, and the stage of liver disease are important factors but, of all the factors involved, the viral population in blood is the most important factor. For example, when the amount of the virus in 1 ml of the patient's blood was less than 1,000,000 copies, the virus could be eliminated from the body and the disease cured by administration of an interferon in about 80% of cases but when the amount of the virus was over 1,000,000 copies, the cure rate was as low as about 9% (Fumio Imazeki et al.: Japanese Journal of Clinics, 53, 1017, 1995).

In addition to the above-mentioned amount of the virus, the inventors of the present invention found that the mode of existence of viral particles in blood is also an important factor modifying the effect of an interferon therapy. Thus, it has been reported that hepatitis C virus particles in blood can be classified according to their suspension density in blood into low-density particles with high infectivity and high-density particles with low infectivity. Therefore, the inventors studied the relationship of those viral particles varying in density to the severity of illness and the interferon therapy and found that whereas the interferon therapy resulted in cure in 75% of patients with the ratio of low-density viral particles to high-density viral particles is 10:1, the cure rate in patients with the ratio of 1:10 was as low as 13%.

It was also found that in blood, the low-density virus particles is bound to lipoprotein and the high-density virus particles to immunoglobulin, thus existing as immune complexes (Akihito Sakai et al.: Japanese Journal of Gastroenterology, 92 (Special Issue), 1488, 1995).

It is, therefore, clear that the contemporary interferon therapy has the drawback that the lower the blood viral population is or the lower the immune-complex virus population is, the higher is the therapeutic response and conversely the higher the viral population is or the hither the immune-complex virus population is, the much lower is the therapeutic response.

SUMMARY OF THE INVENTION

The present invention has for its object to provide an adsorbent for removing hepatitis C virus which has the ability to adsorb hepatitis C virus particles, particularly immune-complex hepatitis C virus particles, from a patient's body blood safely and with high efficiency and high selectivity for enhancing the efficacy of interferon therapy, an hepatitis C virus adsorption apparatus including said adsorbent, and an adsorbing method for removing hepatitis C virus.

For accomplishing the above object, the inventors of the present invention made an intensive exploration for a compound which, when immobilized on a water-insoluble carrier and brought into contact with a patient's blood, should exhibit a high adsorbing affinity for hepatitis C virus but not for such proteins as albumin. As a result, the inventors found that an adsorbent fabricated by immobilizing a compound capable of adsorbing hepatitis C virus, particularly a compound having a binding affinity for immunoglobulin and/or immune complex, on a water-insoluble carrier displays a remarkably high hepatitis C virus-adsorbing performance. The present invention has been developed on the basis of the above finding.

The present invention, therefore, is directed to an adsorbent for removing hepatitis C virus which comprises a compound capable of adsorbing hepatitis C virus as immobilized on a water-insoluble carrier.

BRIEF DESCRIPTION OF THE DRAWINGS

Each numeric symbol represents in the following.
1. outlet
2. inlet
3. absorbent for removing
4,5. means for preventing leakage of the absorbent
6. column
7. apparatus

DETAILED DESCRIPTION OF THE INVENTION

Hereinafter, the present invention is described in detail.

The adsorbent for removing hepatitis C virus according to the present invention comprises a water-insoluble carrier and, as immobilized thereon, a compound capable of adsorbing hepatitis C virus.

The compound capable of adsorbing HCV is not particularly restricted only if it adsorbs hepatitis C virus but the preferred compound has a binding affinity for immunoglobulin and/or immune complex.

The preferred compound, among such compounds capable of adsorbing hepatitis C virus coupled to immunoglobulin and/or immune complex, is a compound which may preferentially and efficiently adsorb hepatitis C virus coupled to immunoglobulin and/or immune complex in comparison with hepatitis C virus particles as such.

More preferably, the above-mentioned compound having a binding affinity for immunoglobulin and/or immune complex is an immunoglobulin-binding protein.

The immunoglobulin-binding protein includes but is not limited to protein A, protein G, protein H, protein L, protein M, rheumatoid factor, and complement.

Still more preferably, the compound having a binding affinity for immunoglobulin and/or immunoglobulin complex is an anti-immunoglobulin antibody.

Even more preferably, the above-mentioned compound capable of adsorbing hepatitis C virus is a component of said immunoglobulin-binding protein and/or anti-immunoglobulin antibody, which component is a fragment protein or a peptide containing a binding site for immunoglobulin and/or immune complex or a derivative of said protein fragment or peptide.

Referring to the water-insoluble carrier, a porous carrier is a preferred example.

Preferably, the porous water-insoluble carrier has a mean pore diameter of from 10 to 1500 nm.

Another preferred form of the water-insoluble carrier is a substantially nonporous carrier. Moreover, the water-insoluble carrier is preferably hydrophilic.

The adsorbent for removing hepatitis C virus according to the present invention can be used for the purpose of removing hepatitis C virus from body fluids inclusive of blood and plasma.

The adsorbent for removing hepatitis C virus can also be used for the purpose of removing immune complex forms of hepatitis C virus from body fluids inclusive of blood and plasma.

The hepatitis C virus adsorption apparatus according to the present invention comprises a casing having an inlet and an outlet for admission and discharge of a fluid and housing any of the above-mentioned adsorbents and a means for preventing leakage of said hepatitis C virus adsorbent from the casing.

The adsorbing method for removing hepatitis C virus comprises a step of contacting any of said adsorbents with a body fluid containing hepatitis C virus.

The HCV-containing body fluid for use in the method for removing HCV according to the present invention includes blood and plasma, among other body fluids.

The preferred embodiments of the invention are now described, although the invention is not limited to those specific embodiments.

The compound capable of adsorbing hepatitis C virus used in the present invention is a compound which is capable of adsorbing hepatitis C virus in a substantial measure and, as such, is not limited in kind. Preferably, however, it is a substance which may specifically bind the heavy chain or light chain of immunoglobulin and/or immunoglobulin complex.

The above-mentioned substance capable of binding the heavy chain or light chain of immunoglobulin and/or immune complex specifically includes the compounds which are generally called immunoglobulin-binding proteins such as protein A, protein G, protein H, protein M, rheumatoid factor, and complement, which can bind the Fc domain in the heavy chain of immunoglobulin G, and protein L which has a binding affinity for the light chain (L. Bjorck: J. Immunol., 140, 1194, 1988; H. Gomi et al.: J. Immunol., 144, 4046, 1990; Hisayuki Doi: Meneki Rinsho (Clinical Immunology), 23, 896, 1991) and anti-immunoglobulin antibodies.

There can also be mentioned those fragments of the above-mentioned substances which have a substantial binding affinity for immunoglobulin and/or immune complex, for example the peptides corresponding to the 58-residue A through E domains, which are immunoglobulin-binding sites, of protein A (M. Uhlen et al.: J. Biol, Chem. 259, 1965, 1984), the FB29 peptide which is a further abridgement of the B domain peptide of protein A (J. S. Huston et al.: Biophysical J., 62, 87, 1992), the peptides corresponding to the 55-residue C1–C3 domains of protein G (B. Guss et al.: EMBO J., 5, 1567, 1986), the A domain peptide of protein H (H. Gomi et al.: ibid), the B1–B5 domain peptides of protein L (Bjorck, Laruth, et al., Japanese Kohyo Publication Hei-7-506573), and the CBP2 peptide of complement C1q (M. A. Baumann et al.: J. Biol. Chem., 265, 18414 (1990), etc., and other immunoglobulin-binding domain peptides of so-called immunoglobulin-binding proteins, and their derivatives.

Furthermore, the Fab and F(ab) 2 fragments of rheumatoid factor or anti-immunoglobulin antibody, single-strand Fv polypeptide, etc. can also be mentioned as representative examples.

The water-insoluble carrier which can be used in the present invention is not particularly restricted but includes inorganic carriers such as glass beads, silica gel, etc., organic carriers such as synthetic polymers, e.g. crosslinked polyvinyl alcohol, crosslinked polyacrylate, crosslinked polyacrylamide, crosslinked polystyrene, etc. and polysaccharides such as crystalline cellulose, crosslinked cellulose, crosslinked agarose, crosslinked dextran, etc., and organic-organic or organic-inorganic composite carriers consisting of such materials.

Particularly preferred are hydrophilic carriers, for such carriers are characterized in that the amount of non-specific adsorption is relatively small and the adsorption selectivity to hepatitis C virus is high. The term "hydrophilic carrier" is used herein to mean a carrier the constituent compound of which has a water-contact angle of not greater than 60 degrees when it is molded in a flat sheet form.

The carrier of this kind is not particularly restricted but includes carriers made of polysaccharides such as cellulose, chitosan, Sepharose, dextran, etc., polyvinyl alcohol, saponified ethylene-vinyl acetate copolymer, polyacrylamide, polyacrylic acid, polymethacrylic acid, poly(methyl methacrylate), polyacrylic acid-polyethylene alloy, polyacrylamide-polyethylene alloy, glass, and so forth.

Particularly, carriers containing OH groups are superior in adsorptive capacity and selectivity. Moreover, porous cellulose gel has the following advantageous features (1)–(4) and, as such, is one of the most preferred carriers for use as the water-insoluble carrier in the practice of the invention.
(1) Because of its comparatively high mechanical strength and toughness, this gel is not easily disintegrated into dust-like fine particles by stirring, etc. and, when packed into a column, it is not appreciably compacted or plugged even when a body fluid is passed through the bed at a high flow rate. Moreover, because of the porous structure, it is not liable to undergo dimensional change even when sterilized by autoclaving.
(2) Because it is made of cellulose, the gel is hydrophilic with a large number of hydroxyl groups available for binding to the ligand and is low in nonspecific adsorption.
(3) Since a comparatively high strength can be retained even if the pore volume is increased, it may have an adsorptive capacity as large as a soft gel.
(4) Compared with synthetic polymer gel or other gels, this gel is higher in safety.

The water-insoluble carriers mentioned above can be used each alone or as a suitable mixture of two or more species.

In consideration of its application as an adsorbent for removing hepatitis C virus and the mode of use, the water-insoluble carrier for use in the present invention preferably has a large surface area and, in this sense, is preferably a carrier having a large number of pores, namely porous.

The preferred mean pore diameter of said porous water-insoluble carrier is between 10 and 1500 nm. Hepatitis C virus particles are 50–55 nm in diameter and in order that such virus particles may be efficiently adsorbed with a porous carrier, the pore size distribution profile of the carrier is preferably biased far toward the range larger than the diameter of virus particles. If the pore diameter is too large, the strength of the carrier will be sacrificed and the surface area decreased. The still more preferred mean particle diameter is between 50 and 1250 nm.

On the other hand, the virus can be adsorbed even with a carrier which is substantially nonporous. This kind of carrier can also be utilized for exploiting the advantage that the proteins and other components useful for the body in the body fluid (blood, plasma, serum, etc.) are little adsorbed in the substantial absence of pores.

The term "substantially nonporous" is used in this specification to include porous carriers having very small pores (e.g. less than 10 nm).

Referring, further, to the porous structure of said water-insoluble carrier, it is preferable, in view of the adsorptive capacity per unit volume of the adsorbent, that the pores should not be confined to the surface but be distributed throughout the carrier and that the carrier has a fractional pore volume of not less than 20% and a specific surface area of not less than 3 $m^2/g$.

The form of said water-insoluble carrier is not particularly restricted but includes bead-form, fibrous form, and film form (inclusive of hollow fiber), among others. From the standpoint of hydrodynamics of the body fluid in extracorporeal circulation, a bead-form carrier is preferably used. As to the mean particle diameter of said bead-form carrier, beads within the range of 10 and 2500 $\mu$m are easy to use. However, it is preferable to use beads in the range of 25 and 800 $\mu$m.

The existence of functional groups available for immobilization of the ligand on the surface of the water-insoluble carrier is beneficial to immobilization.

The representative examples of such functional groups include hydroxyl, amino, aldehyde, carboxyl, thiol, silanol, amido, epoxy, succinylimido, acid anhydride, and other functional groups.

The above-mentioned water-insoluble carrier may be either a rigid gel and a soft gel. For the application as an adsorbent for extracorporeal circulation therapies, it is important that, when packed in a column, there should not occur plugging, i.e. clogging of pores, on passage of a body fluid. Therefore, to insure a sufficient mechanical strength, the water-insoluble carrier is preferably a rigid carrier.

In the context of the present invention, the rigid carrier is a carrier such that when the gel, in the form of e.g. beads, is uniformly packed into a glass cylindrical column (9 mm in. dia., 150 mm long) under the following conditions and an aqueous fluid is passed through the packed column, a linear relationship is obtained between pressure loss ($\Delta P$) and flow rate up to 0.3 $kg/cm^2$.

Figure 1:
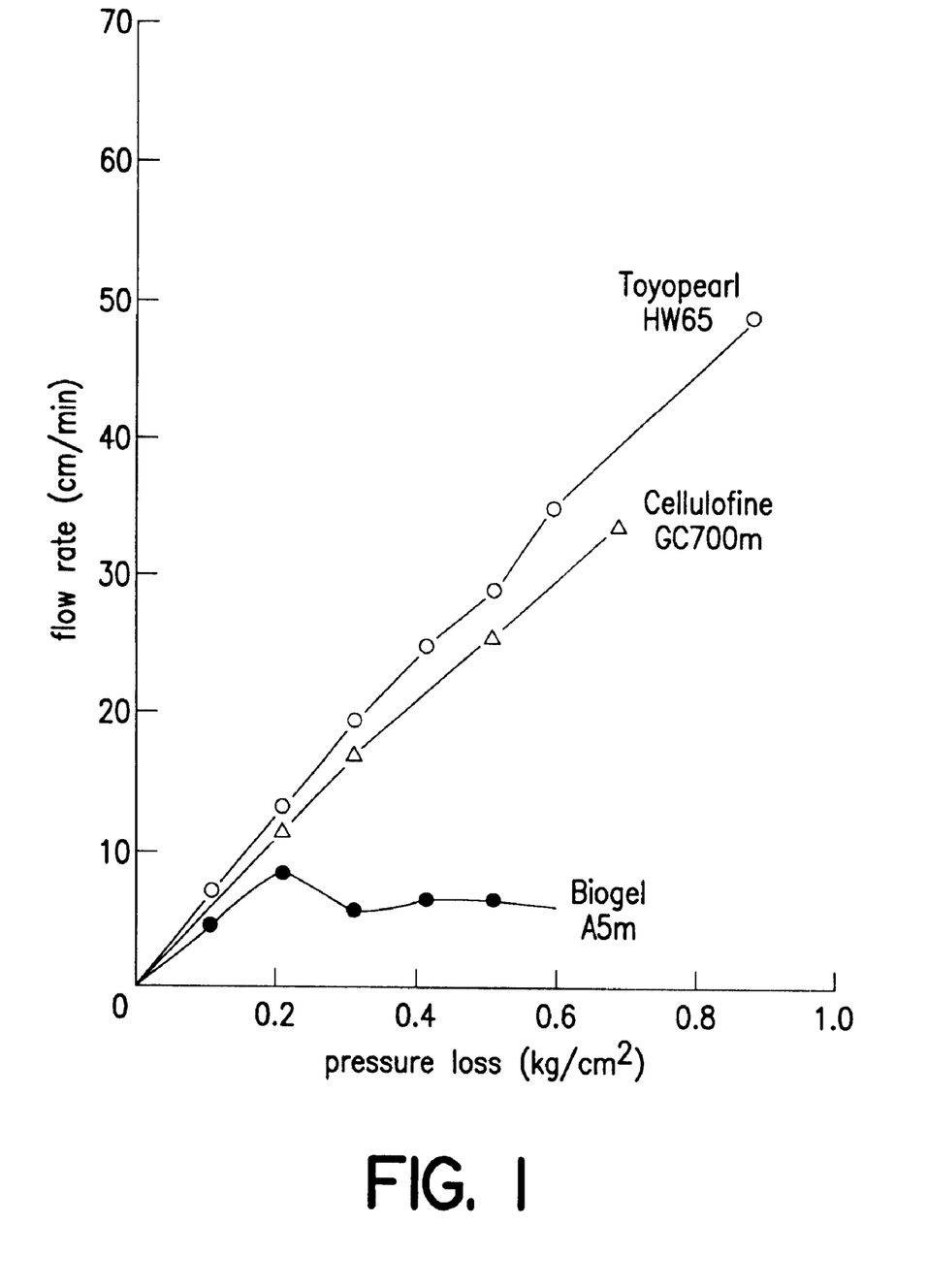
FIG. 1 is a diagrammatic representation of the relation between flow rate and pressure loss for glass columns packed with various water-insoluble carriers. The ordinate represents flow rate (cm/min.) and the abscissa represents pressure loss ($kg/cm^2$)

For example, a glass cylindrical column (9 mm in. dia., 150 mm long) fitted with a 15 $\mu$m (pore diameter) filter at either end was uniformly packed with an agarose gel (Bio-Rad, Biogel-A5m, particle diameter 50–100 mesh), a vinyl polymer gel (Toyo Soda, Toyopearl HW-65, particle diameter 50–1000 $\mu$m), or a cellulose gel (Chisso Corporation, Cellulofine GC-700m, particle diameter 45–105 $\mu$m), water was introduced into the column using a peristatic pump, and the relationship between flow rate and pressure loss ($\Delta P$) was plotted (FIG. 1).

The flow rate (cm/min) was plotted on the ordinate and the pressure loss ($kg/cm^2$) was plotted on the abscissa. In FIG. 1, ○ represents Toyopearl HW-65, Δ represents Cellulofine GC-700m, and ● represents Biogel-A5m.

As a result, whereas the flow rate increased in approximate proportion with an increase in pressure in the case of Toyopearl HW-65 and Cellulofine GC-700m, Biogel-A5m underwent compaction so that the flow rate could not be increased by raising the pressure.

In the immobilization of an immunoglobulin-binding protein or peptide on the water-insoluble carrier in accordance with the present invention, the immobilization is preferably effected through a hydrophilic spacer in order to reduce the steric hindrance of the protein or peptide for improving the adsorption efficiency and suppress non-specific adsorption.

The preferred hydrophilic spacer may for example be a polyalkylene oxide derivative available upon modification of the polyalkylene chain with a substituent group such as carboxyl, amino, aldehyde, or epoxy at either end.

The compound having a binding affinity for immunoglobulin and/or immune complex which is to be immobilized on said water-insoluble carrier and the organic compound as a spacer can be immobilized by any suitable technique. Among such techniques are those which are conventionally used in the immobilization of proteins and peptides on carriers, such as the methods utilizing the epoxy reaction, Nic base reaction, condensation reaction using a carbodiimide reagent, active ester reaction, and carrier crosslinking reaction using glutaraldehyde reagent.

In consideration of the fact that the adsorbent for removing hepatitis C virus according to the invention is an adsorbent chiefly used in extracorporeal circulation therapy and hemocatharsis, it is preferable to use an immobilization method which insures that in the sterilization of the adsorbent and during such therapy, the proteins etc. will not readily be released out from the water-insoluble carrier. For example, the following methods can be mentioned.

(1) The method which comprises reacting the carboxyl group of the carrier with N-hydroxysuccinimide to substitute a succinimidoxycarbonyl group and causing it to react with the amino group of the protein or peptide (active ester method).
(2) The method which comprises subjecting the amino or carboxyl group of the carrier to condensation reaction with the carboxyl or amino group of the protein or peptide in the presence of a condensing agent such as dicyclohexylcarbodiimide (condensation method).
(3) The method in which the protein or peptide is crosslinked using a compound having two or more functional groups, such as glutaraldehyde (carrier crosslinking method).

For suppressing the release and elution of the protein from the carrier, immobilization is preferably effected by covalent bonding.

The adsorbing method for removing hepatitis C virus from a body fluid by contacting a carrier carrying a compound capable of adsorbing hepatitis C virus with a body fluid such as blood, plasma or serum can be practiced in a variety of manners. Specifically, for example, the following methods can be mentioned.

(1) The method which comprises withdrawing a body fluid from the patient's body, pooling it in a bag or the like, mixing the adsorbent with the body fluid there to remove hepatitis C virus, filtering off the adsorbent and returning the substantially hepatitis C virus-free body fluid to the body.
(2) The method which comprises providing a casing having an inlet and an outlet and fitted with a filter permeable to the body fluid but not to the adsorbent across said outlet, packing the casing with the adsorbent, and passing the body fluid through the packed adsorbent.

Although both methods can be selectively employed, the second method (2) is expedient and simple procedure-wise. Moreover, when said casing or column is built into a tubing system for extracorporeal circulation, hepatitis C virus can be efficiently and directly eliminated from the patient's body fluid. The adsorbent for removing hepatitis C virus according to the invention is suited for the latter method.

Figure 2:
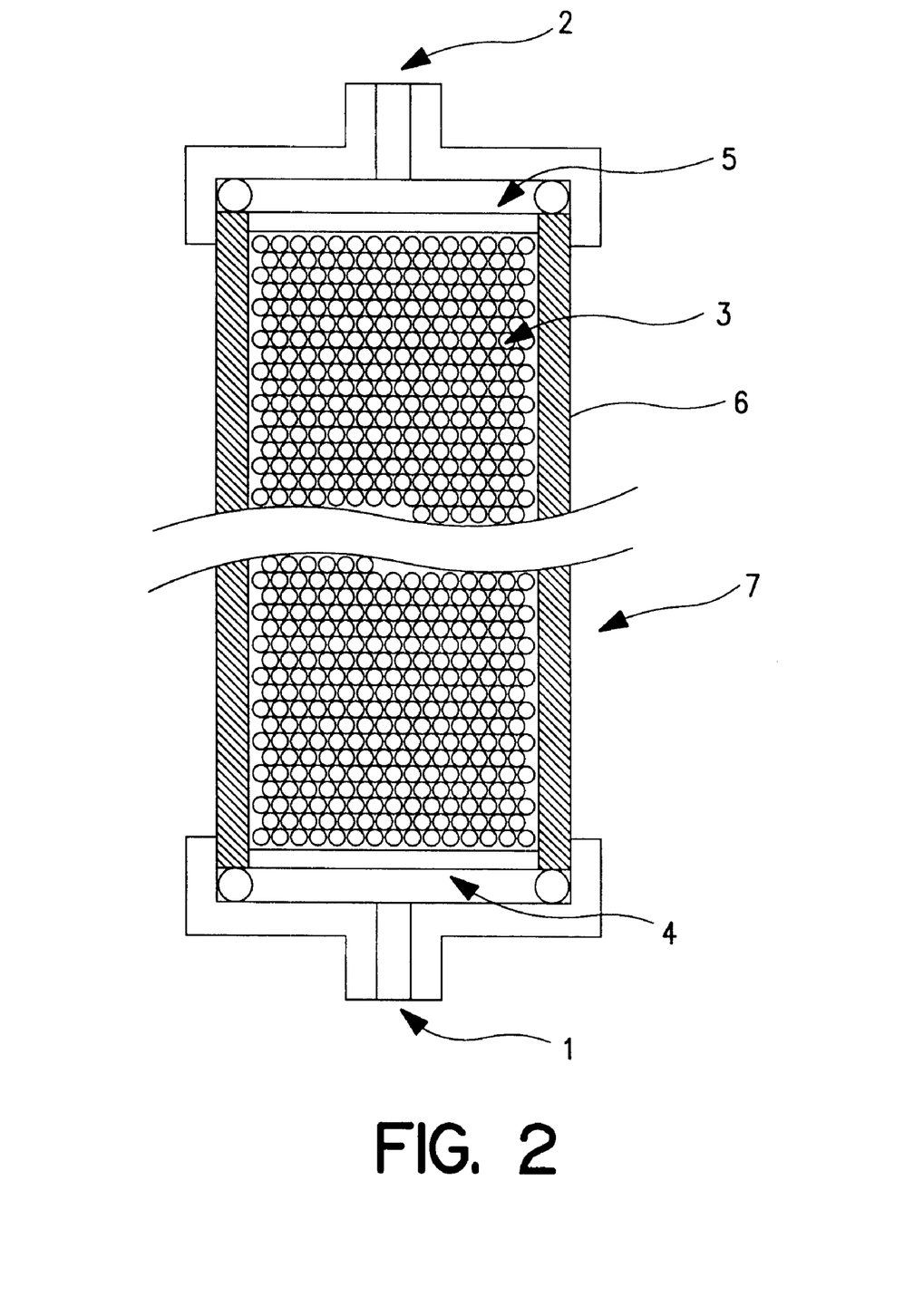
FIG. 2 is a schematic cross-section view of the hepatitis C virus adsorption apparatus according to the invention.

The hepatitis C virus adsorption apparatus including the adsorbent for removing hepatitis C virus according to the invention is now described with reference to the accompanying schematic drawing.

Referring to FIG. 2, the apparatus 7 has a liquid inlet or outlet 1, a liquid outlet or inlet 2, the hepatitis C virus adsorbent of the invention 3, means 4 and 5 for preventing leakage of the adsorbent, through which the body fluid and its components may pass freely but the adsorbent cannot pass, and a column 6.

The geometry and material of the apparatus are not particularly restricted. However, it is preferable to use a cylindrical apparatus having a capacity of about 20–400 mL and a diameter of about 2–10 cm.

BEST MODE FOR CARRYING OUT THE INVENTION

The following examples illustrate the present invention in further detail without delimiting its metes and bounds. In this specification, various amino acid residues are indicated by the following abbreviations.

Ala: L-alanine residue, Asp: L-aspartic acid residue, Asn: L-asparagine residue, Cys: L-cysteine residue, Gln: L-glutamine residue, Glu: L-glutamic acid residue, Gly: L-glycine residue, Ile: L-isoleucine residue, Leu: L-leucine residue, Lys: L-lysine residue, Phe: L-phenylalanine residue, Thr: L-threonine residue, Trp: L-tryptophanresidue, Tyr: L-tyrosine residue, Val: L-valine residue.

In this specification, the amino acid sequence of a peptide is described in the conventional manner, assuming that its amino terminal (hereinafter referred to as N-terminus) is situated at the left end and its carboxyl terminal (referred to as C-terminus) at the right end.

EXAMPLE 1

Immobilization of an IgG-Binding Protein (Protein A) on a Porous Carrier (GCL 2000m)

Expoxy Activation of Cellulose Gel

The cellulosic porous rigid gel GCL-2000m (Chisso Corporation, globular protein cutoff molecular weight $3 \times 10^6$), 90 mL, was made up with water to 180 mL, then 60 mL of 2 M sodium hydroxide was added, and the gel temperature was adjusted to 40° C. To this gel was added 21 mL of epichlorohydrin, and the epoxidation reaction was carried out at 40° C. for 1 hour. After completion of the reaction, the gel was thoroughly rinsed with water to provide an epoxy-activated cellulose gel.

Immobilization of Protein A

In 0.5 mL of 0.05 M borate buffer (pH 10.0) was dissolved 4 mg of protein A (Sigma), and 0.01 N NaOH/water was added so as to bring the pH to 10 and make a total volume of 1.0 mL (protein A solution). This protein solution (total amount) was added to 1 mL of the above epoxy-activated cellulose gel and the mixture was shaken at 37° C. for 16 hours and washed with a sufficient amount of PBS (10 mM phosphate buffer supplemented with 150 mM sodium chloride) to provide GCL 2000m-Protein A.

Quantitation of the Immobilized Protein

The protein A concentration was measured in the reaction mixture by HPLC before and after the immobilization reaction and the reaction rate was calculated to find the amount of immobilization. It was found that 2.1 mg of protein A was immobilized per mL of Protein A-GCL2000m.

EXAMPLE 2

Immobilization of an IgG-Binding Protein (Protein G) on a Porous Carrier (GCL2000m)

Using protein G (Pharmacia LKB) in lieu of protein A, the procedure of Example 1 was otherwise repeated to provide GCL2000m-Protein G (3.2 mg/mL).

EXAMPLE 3

Immobilization of the IgG-Binding Domain of Protein G on a Porous Carrier (Sepharose 6B)

Synthesis of a Peptide

A peptide having the amino acid sequence of 57 residues in the C3 domain of protein G with cysteine added to the N-terminus was synthesized by the solid-phase method using Peptide Synthesizer Model 4170 (Pharmacia LKB).

Using 0.1 mmol of Fmoc-glutamine NovaSyn KA, a resin carrying the C-terminal glutamine, the deprotection reaction and condensation reaction were repeated in the direction toward the N-terminus for peptide chain extension in accordance with the input program of the above peptide synthesizer.

Thus, the cycle of removal of the α-amino-protecting group, i.e. 9-fluorenylmethyloxycarbonyl (Fmoc), from the amino acid with piperidine, washing with dimethylformamide (DMF), the condensation reaction using 2-(1H-benzotriazol-1-yl)-1,1,3,3-tetramethyluronium tetrafluoroborate and diisopropylethylamine, and subsequent washing with DMF was repeated.

The amino acids were used in the forms of Fmoc-L-Ala, Fmoc-L-Asn(Trt), Fmoc-L-Asp(OtBu), Fmoc-L-Cys(Trt), Fmoc-L-Gln(Trt), Fmoc-L-Glu(OtBu), Fmoc-L-Gly, Fmoc-L-Ile, Fmoc-L-Leu, Fmoc-L-Lys(Boc), Fmoc-L-Phe, Fmoc-L-Thr(tBu), Fmoc-L-Trp, Fmoc-L-Tyr(tBu), and Fmoc-L-Val and each in an amount of about 5 molar equivalents (0.5 mmol) based on the substrate in the vial. Here, Trt, OtBu, Boc, and tBu represent trityl, tert-butyl ester, tert-butyloxycarbonyl, and tert-butyl, respectively.

Deprotection and cleavage of the peptide chain

After completion of the reaction series for all the amino acids, the carrier was washed successively with tert-amyl alcohol, acetic acid, and diethyl ether on a 3G-3 pore glass filter and, then, dried in vacuo to provide a dry carrier. To 1 g of the obtained carrier in the vial, 20 mL of trifluoroacetic acid (TFA), 260 μL of 1,2-ethanedithiol, and 780 μL of anisole were added and the mixture was stirred at room temperature for 1.5 hours.

Then, this mixture was filtered through a 3G-3 pore glass filter to remove the carrier and the filtrate was concentrated under reduced pressure at a temperature of 35° C. To the residue was added anhydrous diethyl ether cooled ahead of time until a precipitate ceased to appear under stirring, followed by centrifugation, and the crude peptide pellet was recovered. This crude peptide was rinsed with several portions of anhydrous diethyl ether and dried in vacuo to provide the objective crude peptide.

Purification of the Peptide

The above crude peptide was dissolved in 0.1% TFA and filtered through a 0.2 μm membrane filter and the filtrate was subjected to high performance liquid chromatography. For this HPLC, Model LC-10A System (Shimadzu) and, as the column, μ Bondasphere C18 (Nippon Millipore-Waters) were used in a reversed phase. As the mobile phase, 0.1% TFA/H$_2$O was used as solvent A and 0.1% TFA-80% (v/v) acetonitrile/H$_2$O for solvent B and elution was carried out on a linear gradient from Solvent A to solvent B.

The fraction corresponding to a chromatographic peak was collected. Fractional elution was repeated several times and the pooled fraction was lyophilized to provide a purified peptide. This peptide was subjected to amino acid analysis using Gas-phase Protein Sequencer 477 (Applied Biosystems) and Hitachi Custom Ion Exchange Resin to confirm that the peptide obtained had the amino acid sequence shown in SEQ ID NO:1.

Immobilization of the Peptide

An adsorbent was fabricated by immobilizing the above peptide on a porous Sepharose as follows. As the Sepharose, Thiopropyl-Sepharose 6B (Pharmacia LKB) was used. To 50 mg of Thiopropyl-Sepharose 6B was added 5 ml of distilled water and the mixture was plated at room temperature for 15 minutes to let the resin swell. Then, distilled water was removed and replaced with 0.5 M NaCl-0.1 M Tris-HCl (pH 7.5) coupling buffer.

On the other hand, 4 mg of the above purified peptide was dissolved in 400 μL of 0.5 M NaCl-0.1 M Tris-HCl (pH 7.5) coupling buffer. To this solution was added 150 μL of the above swollen Thiopropyl-Sepharose 6B, and the mixture was stirred at 4° C. for 12 hours, whereby an adsorbent carrying the purified peptide was obtained.

This peptide-carrying adsorbent was suction-filtered and the peptide content in the filtrate was determined by HPLC using the absolute calibration curve method to find the peptide immobilization rate. This peptide-carrying adsorbent was washed well with 150 mM NaCl-10 mM phosphate buffer (pH 7.2) and suction-filtered to recover Sepharose 6B-C3Ppt carrying 3.6 mg of the peptide per mL of the carrier.

EXAMPLE 4

Immobilization of an IgG-Binding Peptide (MK3P47) on a Porous Carrier (Kac)

Production of MK3P47 Peptide

A DNA coding for the MK3P47 peptide having the amino acid sequence shown in SEQ ID NO:2 was designed and synthesized so that it could be ligated to pUCNT Vector (Japanese Kokai Publication Hei-4-212692) by utilizing its Nde I restriction enzyme site for the 5'-end and its Hind III restriction enzyme site for the 3'-end. The nucleotide sequence of the synthesized DNA is shown in SEQ ID NO:3.

Figure 3:
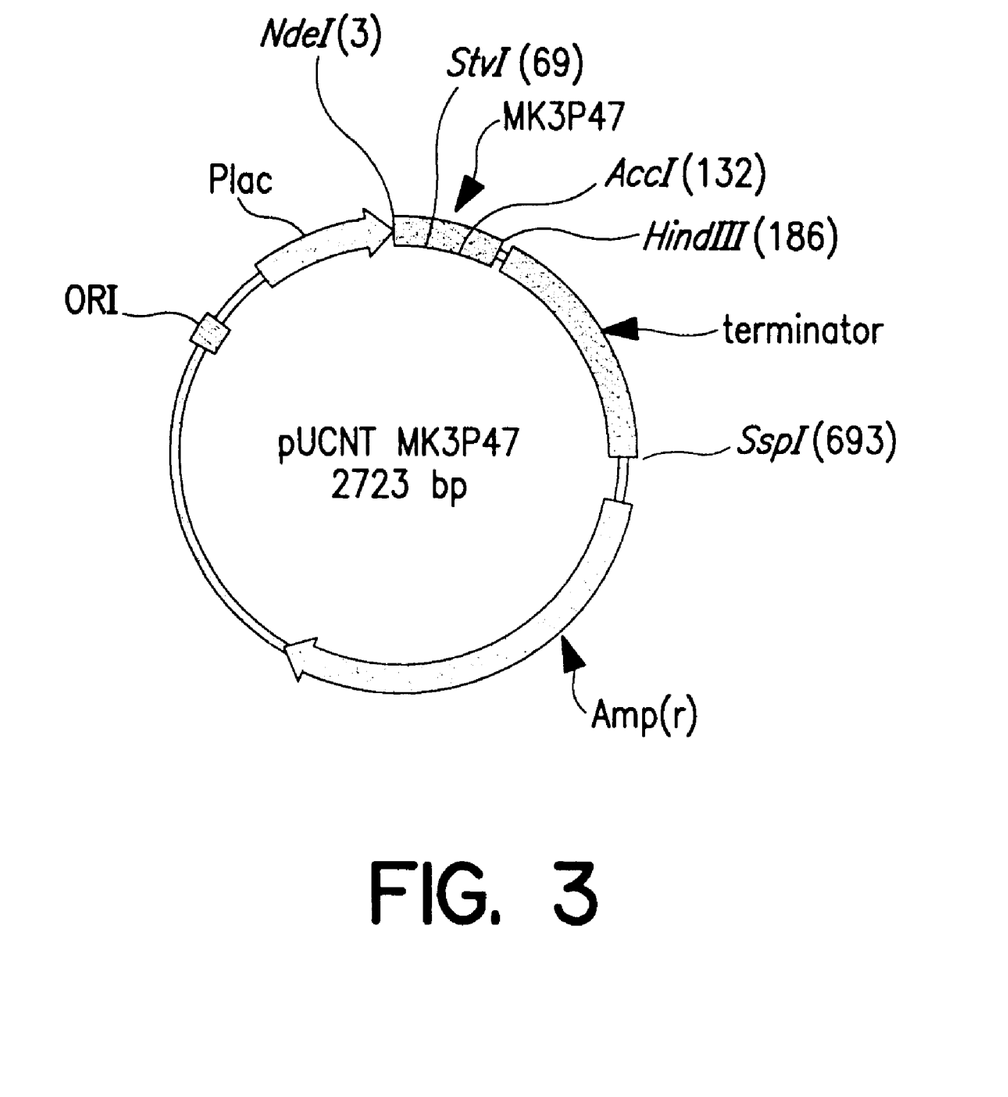
FIG. 3 is a diagram showing the pUCNTMK3P47 vector.

The DNA having the above sequence was ligated to pUCNT Vector cleaved with the restriction enzymes Nde I and Hind III (Takara Shuzo) in accordance with the manual of Takara Shuzo's DNA Ligation Kit Ver. 2 to construct a pUCNTMK3P47 vector (FIG. 3).

Then, using the known technique, this pUCNTMK3P47 vector DNA was subcloned in *Escherichia coli* HB101 (Irivitrogen) and a transformant was selected with resistance to the antibiotic ampicillin as an indicator.

From this transformant, the plasmid DNA was extracted and sequenced by the conventional procedure to confirm that it had a DNA sequence conforming to the pUCNTMK3P47 vector design.

Then, this transformant was shake-cultured in 6L of L-Broth (5 g/L NaCl, 10 g/L Bactotrypsin, 5 g/L yeast extract) at 37° C. for 20 hours and the cells were recovered by centrifugation (Hitachi RPR9-2 rotor, 4° C., 6000 rpm× 20 min.).

The pellet obtained was suspended in 300 mL of TE Buffer (20 mM Tris-HCl, 1 mM EDTA; pH 7.5), sonicated (BPANSON 250, in ice, 6 min.×3), and centrifuged (Hitachi RPR16 rotor, 4° C., 15000 rpm×20 min.) and the supernatant was recovered.

The above supernatant was heat-treated at 70° C. for 10 minutes and then recentrifuged (Hitachi RPR16 rotor, 4° C., 15000 rpm×20 min.) to provide 300 mL of a supernatant. From this supernatant, the objective MK3P47 peptide was isolated as follows. Using a high performance liquid chromatograph (column: Waters' μBONDASPHERE 5μ C18 300A, 19.0×150 mm), 40 ml of acetonitrile was passed at a flow rate of 5 ml/min to activate the column and, then, 300 mL of the sample was passed at the same flow rate. The column was washed with 200 mL of 0.1% TFA+64% acetonitrile and the objective MK3P47 peptide was then eluted with 200 mL of 0.1% TFA+40% acetonitrile.

This fraction was concentrated to 100 mL on an evaporator and lyophilized to provide 1.2 g of a high-purity sample of the peptide.

Expoxy Activation of Cellulose Gel

The prototype cellulosic porous rigid gel Kac with a globular protein cutoff molecular weight of >5×10$^6$, prepared by the present applicant, 90 mL, was made up with water to 180 mL. Then, 60 mL of 2 M sodium hydroxide was added and the gel temperature was increased to 40° C. To this gel was added 21 mL of epichlorohydrin and the reaction was conducted at 40° C. with stirring for 1 hour. After completion of the reaction, the gel was thoroughly rinsed with water to provide an epoxy-activated cellulose gel.

Immobilization of MK3P47 and determination of the amount of immobilized protein

Except that 50 mg of MK3P47 was used in lieu of 4 mg of protein A and epoxy-activated Kac was used in lieu of epoxy-activated GCL-2000m, the procedure of Example 1 was otherwise repeated to provide Kac-MK3P47 (30 mg/mL).

EXAMPLE 5

Immobilization of an IgG-Binding Peptide (MP47C) on Aporous Carrier (Sephacryl S1000)

Peptide MP47C having the amino acid sequence shown in SEQ ID NO:4 was prepared.

A DNA (coding for MP47C) of the nucleotide sequence shown in SEQ ID NO:5 was designed and synthesized so that it could be ligated to pUCNT Vector as in Example 4.

Thus, a pUCNTMP47C vector was prepared by ligating the above DNA to pUCNT Vector by the same procedure as in Example 4.

Then, in the same manner as described in Example 4, an *E. coli* transformant was constructed and from 6L of its culture, 1.3 g of a high-purity sample of the objective peptide was obtained and used in various studies.

Epoxy Activation of Sephacryl Gel

The cellulosic porous rigid gel (pore diameter 400 nm) Sephacryl S1000 (Pharmacia LKB), 90 mL, was made up with water to 180 mL. Then, 60 mL of 2M sodium hydroxide was added and the gel temperature was increased to 40° C. To this gel was added 21 mL of epichlorohydrin and the reaction was conducted at 40° C. with stirring for 1 hour. After completion of the reaction, the gel was thoroughly rinsed with water to provide an epoxy-activated Sephacryl gel.

Immobilization of MP47C and determination of the amount of immobilized protein

Except that 10 mg of MP47C was used in lieu of 4 mg of protein A and the epoxy-activated Sephacryl gel was used in lieu of epoxy-activated GCL-2000m, the procedure of Example 1 was otherwise repeated to provide S1000-MP47C (7 mg/mL).

EXAMPLE 6

Immobilization of an IgG-Binding Peptide (MP47C) on a Substantially Nonporous Carrier (Bac)

Epoxy Activation of Cellulose Gel

The prototype cellulosic rigid gel nonporous carrier (Bac) with a globular protein cutoff molecular weight of <3×10$^4$, 90 mL, was made up to 180 mL with water. Then, 60 mL of 2 M sodium hydroxide was added and the gel temperature was increased to 40° C. To this gel was added 21 mL of epichlorohydrin, and the reaction was carried out at 40° C. with stirring for 1 hour. After completion of the reaction, the gel was thoroughly rinsed with water to provide an epoxy-activated cellulose gel.

Immobilization of MP47C and determination of the amount of immobilized protein

Except that 30 mg of MP47C was used in lieu of 4 mg of protein A and epoxy-activated Bac in lieu of epoxy-activated GCL-2000m, the immobilization procedure of Example 1 was otherwise repeated to provide Bac-MP47C (20 mg/mL).

EXAMPLE 7

Immobilization of a Fragment (Fab) of the Anti-IgG Antibody on a Porous Carrier (CNBr-Activated Sepharose 6B)

CNBr-activated Sepharose 4B (Pharmacia LKB), 4 g, was swollen with a small amount of 1 mM HCl/H$_2$O for 15 minutes and washed with 1 mM HCl/H$_2$O and coupling buffer (pH 8.3, 0.5 M NaCl, 0.1 M NaHCO$_3$) in that order.

In 1 mL of coupling buffer was dissolved 1 mg of the Fab available on papaine digestion (PIECE, ImmunoPure Fab Preparation Kit) of anti-human IgG (Fab) antibody (Binding Site Co.). To this solution was added the above washed gel and the reaction was carried out at 4° C. for 16 hours.

After the reaction mixture was washed with coupling buffer, block buffer (pH 8.3, 0.2 M glycine, 0.5 M NaCl, 0.1 M NaHCO$_3$) was added and reacted at room temperature for 2 hours.

The reaction product was washed with two kinds of after-treatment buffers (pH 4.0, 0.5 M NaCl, 0.1 M acetic acid-sodium acetate buffer and pH 8.0, 0.5 M NaCl, 0.1 M Tris-HCl buffer) alternately 3 times each to provide Sepharose 4B-Anti-IgG Fab.

EXAMPLE 8

Immobilization of the Anti-IgG Antibody on a Porous Carrier (tresyl Toyopearl)

The anti-human IgG (Fc) antibody (Binding Site Co.), 1 mg, was dissolved in 1 mL of coupling buffer (0.5 M NaCl, 0.1 M carbonate buffer) followed by addition of 200 mg of dry AF-tresyl-Toyopearl 650. The reaction was carried out at 4° C. overnight.

After the reaction product was washed with 0.5 M NaCl/water, block buffer (pH 8.0, 0.5 M NaCl, 0.1 M Tris-HCl buffer) was added and reacted at room temperature for 2 hours.

This reaction mixture was further washed with 0.5 M NaCl/H$_2$O to provide Toyopearl-anti-IgG.

EXAMPLE 9

Evaluation for the Hepatitis C Virus-Adsorbing Performance of the Synthesized Adsorbents Adsorption Experiment Each adsorbent, 100 μL, was taken in a vial, 100 μl of a patient serum containing hepatitis C virus was added, and the mixture was shaken at 37° C. for 2 hours.

Determination of hepatitis C virus-adsorbing capacity

The above suspension was centrifuged at 5000 rpm for 1 minute and the amount of hepatitis C virus in the supernatant was determined as HCV RNA (Nippon Roche, Amplicore HCV Monitor).

As a control experiment, 100 μL of physiological saline in lieu of the adsorbent was taken in a vial and the above procedure was repeated to determine the amount of hepatitis C virus in the solution.

The adsorption rate (%) of hepatitis C virus was calculated by means of the following equation.

Adsorption rate (%)=[(Vr−Vt)/Vr]×100

Vr: concentration of the virus in control solution

Vt: concentration of the virus in adsorption test supernatant

The results are shown in Table 1.

TABLE 1

| Example | Adsorbent | HCV RNA adsorption test supernatant (copy/mL) | HCV RNA control solution (copy/mL) | Adsorption rate (%) |
|---|---|---|---|---|
| 1 | GCL2000m-Protein A | 2.70E+04 | 7.90E+04 | 66 |
| 2 | GCL2000m-Protein G | 1.40E+04 | 7.90E+04 | 82 |
| 3 | Sepharose6B-C3Ppt | 8.10E+04 | 1.12E+05 | 28 |
| 4 | Kac-MK3P47 | 3.20E+04 | 1.05E+05 | 70 |
| 5 | S1000-MP47C | 1.00E+04 | 1.05E+05 | 91 |
| 6 | Bac-MP47C | 4.20E+04 | 1.05E+05 | 60 |
| 7 | Sepharose4B-AntiIgGFab | 4.80E+04 | 1.05E+05 | 54 |
| 8 | Toyopearl-AntiIgG | 3.60E+04 | 1.05E+05 | 66 |

EXAMPLE 10

Evaluation of the Synthesized Adsorbents

Adsorption Test

Each adsorbent, 100 μL, was taken in a vial, 100 μL of hepatitis C virus-containing patient serum was added, and the mixture was shaken at 37° C. for 2 hours.

Determination of high-density HCV/low-density HCV

The HCV suspension obtained in each adsorption experiment and the HCV suspension obtained using physiological saline in lieu of the adsorbent in otherwise the same manner were respectively admixed with anti-LDL and anti-IgG antibodies and the reaction was carried out at 4° C. for 16 hours. The reaction mixture was centrifuged at 5000 rpm for 15 minutes, the pellet was recovered, and the amount of hepatitis C virus was determined as HCV RNA (Nippon Roche, Amplicore HCV Monitor). Regarding the HCV precipitated by anti-LDL antibody as low-density HCV and the HCV precipitated by anti-IgG antibody as high-density HCV, the HCV RNA ratio (T/B=low-density HCV/high-density HCV) was calculated.

The results are shown in Table 2.

TABLE 2

| Example | Adsorbent | T/B HCV adsorption experiment | T/B HCV control experiment |
|---|---|---|---|
| 1 | GCL2000m-Protein A | 3/1 | 1/1 |
| 2 | GCL2000m-Protein G | 2/1 | 1/1 |
| 3 | Sepharose6B-C3Ppt | 3/2 | 1/1 |
| 4 | Kac-MK3P47 | 1/1 | 1/10 |
| 5 | S1000-MP47C | 1/1 | 1/10 |
| 6 | Bac-MP47C | 1/5 | 1/10 |
| 7 | Sepharose4B-AntiIgGFab | 1/3 | 1/10 |
| 8 | Toyopearl-AntiIgG | 1/3 | 1/10 |

INDUSTRIAL APPLICAPABILITY

As is clear from the following examples, the present invention provides a novel adsorbent having the ability to selectively adsorb and remove the hepatitis C virus present in body fluids and/or the ability to reduce the ratio of high-density HCV to low-density HCV. Furthermore, by using a body fluid treating apparatus packed with the above adsorbent, hepatitis C virus can be selectively removed from body fluids such as blood, plasma, and serum.

---

What is claimed is:

1. An adsorbent for removing hepatitis C virus which comprises a compound capable of adsorbing hepatitis C virus as immobilized on a water-insoluble carrier, wherein the compound capable of adsorbing hepatitis C virus is, a peptide having the amino acid sequence of SEQ ID NO:1, SEQ ID NO:2, or SEQ ID NO:4.

2. The adsorbent for removing hepatitis C virus according to claim 1 wherein the water-insoluble carrier is a porous carrier.

3. The adsorbent for removing hepatitis C virus according to claim 2, wherein the porous carrier has a mean pore diameter ranging from 10 to 1500 nm.

4. The adsorbent of claim 3 wherein the carrier has a fractional pore volume of not less than 20% and a specific surface area of not less than 3m²/g.

5. The adsorbent for removing hepatitis C virus according to claim 1, wherein the water-insoluble carrier is a substantially nonporous carrier.

6. The adsorbent for removing hepatitis C virus according to claim 1 wherein the water-insoluble carrier is a hydrophilic carrier.

7. An apparatus for adsorbing hepatitis C virus which comprises a casing having an inlet and an outlet for admission and discharge of a fluid and housing the adsorbent for removing hepatitis C virus according to claim 1, and a means for preventing leakage of said adsorbent for removing hepatitis C virus from the casing.

8. The adsorbent for removing hepatitis C virus according to claim 1 wherein the compound capable of adsorbing hepatitis C virus is a peptide having the amino acid sequence of SEQ ID NO:1.

9. The adsorbent for removing hepatitis C virus according to claim 1 wherein the compound capable of adsorbing hepatitis C virus is a peptide having the amino acid sequence of SEQ ID NO:2.

10. The adsorbent for removing hepatitis C virus according to claim 1 wherein the compound capable of adsorbing hepatitis C virus is a peptide having the amino acid sequence of SEQ ID NO:4.

11. An adsorbent for removing hepatitis C virus which comprises a compound capable of adsorbing hepatitis C virus bound to immunoglobulin and/or immune complex as immobilized on a water-insoluble carrier, wherein said compound capable of adsorbing hepatitis C virus is bound to immunoglobulin and/or immune complex is a peptide having the amino acid sequence of SEQ ID NO:1, SEQ ID NO:2, or SEQ ID NO:4.

12. The adsorbent for removing hepatitis C virus according to claim 11 wherein the water-insoluble carrier is a porous carrier.

13. The adsorbent for removing hepatitis C virus according to claim 12 wherein the porous carrier has a mean pore diameter ranging from 10 to 1500 nm.

14. The adsorbent for removing hepatitis C virus according to claim 13 wherein the carrier has a fractional pore volume of not less than 20% and a specific surface area of not less than 3 m²/g.

15. The adsorbent for removing hepatitis C virus according to claim 11 wherein the water-insoluble carrier is a substantially nonporous earner.

16. The adsorbent for removing hepatitis C virus according to claim 11 wherein the water-insoluble carrier is a hydrophilic carrier.

17. An apparatus for adsorbing hepatitis C virus which comprises a casing having an inlet and an outlet for admission and discharge of a fluid and housing the adsorbent for removing hepatitis C virus according to claim 11, and a means for preventing leakage of said adsorbent for removing hepatitis C virus from the casing.

18. The adsorbent for removing hepatitis C virus according to claim 11 wherein the compound capable of adsorbing hepatitis C virus bound to immunoglobulin and/or immune complex is a peptide having the amino acid sequence of SEQ ID NO:1.

19. The adsorbent for removing hepatitis C virus according to claim 11 wherein the compound capable of adsorbing hepatitis C virus bound to immunoglobulin and/or immune complex is a peptide having the amino acid sequence of SEQ ID NO:2.

20. The adsorbent for removing hepatitis C virus according to claim 11 wherein the compound capable of adsorbing hepatitis C virus bound to immunoglobulin and/or immune complex is a peptide having the amino acid sequence of SEQ ID NO:4.

* * * * *

UNITED STATES PATENT AND TRADEMARK OFFICE
CERTIFICATE OF CORRECTION

PATENT NO. : 6,600,014 B2  
DATED : July 29, 2003  
INVENTOR(S) : Eiji Ongino et al.

It is certified that error appears in the above-identified patent and that said Letters Patent is hereby corrected as shown below:

<u>Column 18,</u>  
Line 30, the word "earner" should be replaced with -- carrier --

Signed and Sealed this

Twenty-seventh Day of January, 2004

JON W. DUDAS  
*Acting Director of the United States Patent and Trademark Office*

SEQUENCE LISTING

<160> NUMBER OF SEQ ID NOS: 5

<210> SEQ ID NO 1
<211> LENGTH: 58
<212> TYPE: PRT
<213> ORGANISM: Artificial Sequence
<220> FEATURE:
<223> OTHER INFORMATION: lgG - binding domain of protein G

<400> SEQUENCE: 1

Cys Thr Thr Tyr Lys Leu Val Ile Asn Gly Lys Thr Leu Lys Gly Glu
1               5                   10                  15

Thr Thr Thr Lys Ala Val Asp Ala Ala Glu Thr Ala Glu Lys Ala Phe
            20                  25                  30

Lys Gln Tyr Ala Asn Asp Asn Gly Val Asp Gly Val Trp Thr Tyr Asp

```
                35                  40                  45

Asp Ala Thr Lys Thr Phe Thr Val Thr Glu
    50                  55
```

<210> SEQ ID NO 2
<211> LENGTH: 60
<212> TYPE: PRT
<213> ORGANISM: Artificial Sequence
<220> FEATURE:
<223> OTHER INFORMATION: lgG - binding peptide

<400> SEQUENCE: 2

```
Met Lys Lys Lys Thr Thr Tyr Lys Leu Val Ile Asn Gly Lys Thr Leu
1               5                   10                  15

Lys Gly Glu Thr Thr Thr Lys Ala Val Asp Ala Glu Thr Ala Glu Lys
            20                  25                  30

Ala Phe Lys Gln Tyr Ala Asn Asp Asn Gly Val Asp Gly Val Trp Thr
        35                  40                  45

Tyr Asp Pro Ala Thr Lys Thr Phe Thr Val Thr Glu
    50                  55                  60
```

<210> SEQ ID NO 3
<211> LENGTH: 190
<212> TYPE: DNA
<213> ORGANISM: Artificial Sequence
<220> FEATURE:
<223> OTHER INFORMATION: DNA coding for Sequence ID No: 2

<400> SEQUENCE: 3

```
catatgaaaa agaagaccac ctataaactg gttatcaacg gtaaaaccct gaaaggtgaa      60
accaccacca aggctgttga cgctgaaacc gctgaaaaag catttaaaca gtatgctaac     120
gacaacggtg tcgacggtgt ttggacctat gaccccgcta ccaaaacctt taccgttacc     180
gaataagctt                                                            190
```

<210> SEQ ID NO 4
<211> LENGTH: 58
<212> TYPE: PRT
<213> ORGANISM: Artificial Sequence
<220> FEATURE:
<223> OTHER INFORMATION: lgG - binding peptide

<400> SEQUENCE: 4

```
Met Thr Thr Tyr Lys Leu Val Ile Asn Gly Lys Thr Leu Lys Gly Glu
1               5                   10                  15

Thr Thr Thr Lys Ala Val Asp Ala Glu Thr Ala Glu Lys Ala Phe Lys
            20                  25                  30

Gln Tyr Ala Asn Asp Asn Gly Val Asp Gly Val Trp Thr Tyr Asp Pro
        35                  40                  45

Ala Thr Lys Thr Phe Thr Val Thr Glu Cys
    50                  55
```

<210> SEQ ID NO 5
<211> LENGTH: 184
<212> TYPE: DNA
<213> ORGANISM: Artificial Sequence
<220> FEATURE:
<223> OTHER INFORMATION: DNA coding for Sequence ID No. 4

<400> SEQUENCE: 5

```
catatgacca cctataaact ggttatcaac ggtaaaaccc tgaaaggtga aaccaccacc      60
```

-continued

```
aaggctgttg acgctgaaac cgctgaaaaa gcatttaaac agtatgctaa cgacaacggt    120
gtcgacggtg tttggaccta tgacccgct  accaaaacct ttaccgttac cgaatgctaa    180
gctt                                                                 184
```